(12) United States Patent
Avinash et al.

(10) Patent No.: US 7,702,379 B2
(45) Date of Patent: Apr. 20, 2010

(54) SYSTEM AND METHOD FOR HYBRID TRACKING IN SURGICAL NAVIGATION

(75) Inventors: Gopal B. Avinash, New Berlin, WI (US); Allison Leigh Weiner, Milwaukee, WI (US); Peter Traneus Anderson, Andover, MA (US)

(73) Assignee: General Electric Company, Schenectady, NY (US)

( * ) Notice: Subject to any disclaimer, the term of this patent is extended or adjusted under 35 U.S.C. 154(b) by 1327 days.

(21) Appl. No.: 10/926,380

(22) Filed: Aug. 25, 2004

(65) Prior Publication Data

US 2006/0058604 A1    Mar. 16, 2006

(51) Int. Cl.
*A61B 5/05* (2006.01)
(52) U.S. Cl. ...................... 600/424; 378/116
(58) Field of Classification Search ......... 600/424–429; 378/116
See application file for complete search history.

(56) References Cited

U.S. PATENT DOCUMENTS

| | | | |
|---|---|---|---|
| 736,432 A | | 8/1903 | Owens |
| 4,993,404 A | * | 2/1991 | Lane .......................... 600/109 |
| 5,831,260 A | | 11/1998 | Hansen |
| 5,891,034 A | * | 4/1999 | Bucholz ..................... 600/426 |
| 5,917,883 A | * | 6/1999 | Khutoryansky et al. ..... 378/116 |
| 5,930,741 A | | 7/1999 | Kramer |
| 5,953,683 A | | 9/1999 | Hansen et al. |
| 6,129,667 A | | 10/2000 | Dumoulin et al. |
| 6,235,038 B1 | | 5/2001 | Hunter et al. |
| 6,288,785 B1 | | 9/2001 | Frantz et al. |
| 6,361,507 B1 | | 3/2002 | Foxlin |
| 6,369,564 B1 | | 4/2002 | Khalfin et al. |
| 6,574,498 B1 | | 6/2003 | Gilboa |
| 7,049,594 B2 | * | 5/2006 | Wu et al. .................. 250/338.1 |
| 2001/0011175 A1 | | 8/2001 | Hunter et al. |

FOREIGN PATENT DOCUMENTS

EP    1 518 508    3/2005

OTHER PUBLICATIONS

Schwald, Bernd and Seibert, Helmut, "Registration Tasks for a Hybrid Tracking System for Medical Augmented Reality", Journal of WSCG, vol. 12, No. 1-3, Feb. 2-6, 2004, UNION Agency—Science Press.

* cited by examiner

*Primary Examiner*—Long V Le
*Assistant Examiner*—Saurel J Selkin
(74) *Attorney, Agent, or Firm*—McAndrews, Held & Malloy, Ltd.; Peter J. Vogel; Michael A. Dellapenna

(57) ABSTRACT

A system and method for hybrid tracking in surgical navigation is disclosed. A plurality of tracking technologies is used in a medical procedure where a reconciler determines an active tracking technology. The reconciler determines the active tracking technology during the medical procedure. A switch may then activate one or more tracking technologies. The determination of which technology or technologies are to be activated may be based, for example, on metrics measured by each of the technologies, such as an accuracy measurement. In addition, a display may present representations based on at least data obtained by one or more of the tracking technologies. The switch may employ weighted switching to gradually switch the display of a first representation corresponding to a first tracking technology to the display of a second representation corresponding to a second tracking technology, where the first technology is deactivated and the second technology is activated.

24 Claims, 5 Drawing Sheets

SYSTEM AND METHOD FOR HYBRID TRACKING IN SURGICAL NAVIGATION

BACKGROUND OF THE INVENTION

The present invention generally relates to navigation in a medical procedure. Specifically, the present invention provides a system and method for hybrid tracking in surgical navigation.

Medical practitioners, such as doctors, surgeons, and other medical professionals, often rely upon tracking or navigation systems when performing a medical procedure. Such systems may provide positioning and/or orientation ("P&O") information for a medical instrument or implant with respect to the patient or a reference coordinate system, for example. A medical practitioner may refer to the tracking system to ascertain the P&O of the medical instrument when the instrument is not within the practitioner's line of sight with regard to the patient's anatomy, or with respect to non-visual information relative to the patient. A tracking system may also aid in pre-surgical planning.

A tracking system allows the medical practitioner to visualize the patient's anatomy and track the P&O of the instrument. The medical practitioner may use the tracking system to determine when the instrument or implant is positioned in a desired location or oriented in a particular direction. The medical practitioner may locate and operate on, or provide therapy to, a desired or injured area while avoiding other structures. Increased precision in locating medical instruments within a patient may provide for a less invasive medical procedure by facilitating improved control over smaller, flexible instruments having less impact on the patient. Improved control and precision with smaller, more refined instruments may also reduce risks associated with more invasive procedures such as open surgery.

Tracking systems may be optical, ultrasonic, inertial, electromagnetic, or sonic, for example. Generally, each system includes its own advantages and disadvantages. For example, optical tracking is typically considered the most accurate tracking technology. However, optical tracking requires a line-of-sight. During the course of a surgical procedure, a line-of-sight path may become impossible to achieve. If the surgeon relies on optical tracking alone, navigation of the instrument or implant may be temporarily unavailable.

At such a point during a medical procedure, the surgeon may wish to employ another tracking technology, such as an electromagnetic tracking system. Electromagnetic tracking systems allow for a surgeon to track a position and/or orientation of one sensor relative to another, without requiring a line-of-sight. However, due to electromagnetic interference caused by, among other things, metal objects in the operating environment, electromagnetic tracking systems may not always be the most accurate of the available tracking systems. Thus, at another point during the procedure, the surgeon may wish to again switch from the electromagnetic tracking system to another system.

While some current systems and methods may allow for a surgeon to employ more than one tracking technology during a medical procedure, such systems and methods typically do not allow for a dynamic change of tracking technologies. In other words, most of such systems and methods may allow for a surgeon to determine, before a medical procedure begins, which tracking technologies are to be used during the procedure.

However, current systems and methods do not allow for a surgeon to switch from one tracking technology to another "on the fly." In other words, at some point during a procedure, one or more unused tracking technologies may be more accurate than the currently used technology. At that point, the surgeon may wish to switch from the currently used technology to one or more of the unused technologies. The surgeon may therefore ensure that he or she is constantly and consistently utilizing one of the most accurate tracking systems available to the surgeon.

Thus, a need exists for a system and method for hybrid tracking in surgical navigation. Such a system and method can provide for dynamic switching between two or more tracking technologies during a medical procedure to assist in the accuracy of navigation during a medical procedure.

BRIEF SUMMARY OF THE INVENTION

The present invention provides a medical tracking system. The system includes a plurality of tracking technologies employed in a medical procedure, a reconciler determining an active tracking technology during said procedure and a switch activating said active tracking technology. The active tracking technology includes at least one of the tracking technologies.

The present invention also provides a method for hybrid tracking in medical navigation system. The method includes employing a plurality of tracking technologies for use in a medical procedure, determining an active tracking technology during said procedure, and activating the active tracking technology. The active tracking technology includes at least one of said tracking technologies.

The present invention also provides a system for optimizing an accuracy of navigation in a medical procedure. The system includes first and second tracking systems used in the procedure, a monitor measuring first and second accuracies of the first and second tracking systems, respectively, and a switch activating the first tracking system and deactivating the second tracking system when the first accuracy measurement is greater than the second accuracy measurement.

Figure 1:
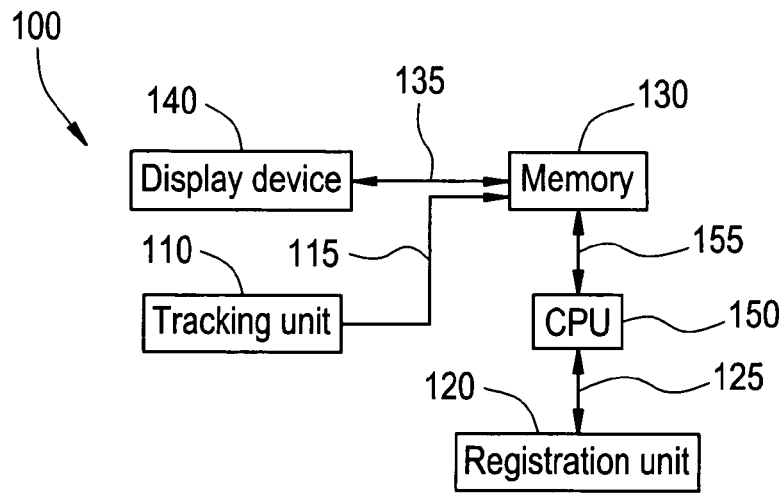
FIG. 1 illustrates a hybrid tracking system for surgical navigation used in accordance with an embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

FIG. 1 illustrates a hybrid tracking system 100 for surgical navigation used in accordance with an embodiment of the present invention. System 100 includes a tracking unit 110, a registration unit 120, a memory 130, a display device 140 and a computer ("CPU") 150. Tracking unit 110 is in communication with memory 130. Registration unit 120 is in communication with CPU 150. Memory 130 is in communication with tracking unit 110, display device 140, and CPU 150. Display device 140 is in communication with memory 130. CPU 150 is in communication with registration unit 120 and memory 130.

In operation, tracking unit 110 can be employed in a medical procedure to obtain tracking data 115. For example, tracking unit 110 can obtain a position and/or orientation of a medical device or implant relative to some reference point. However, tracking data 115 can include additional information, such as stress and/or pressure measurements, time measurements, and image data used to create an image, for example.

In addition, as described in more detail below, tracking unit 110 may obtain tracking data 115 from a plurality of tracking technologies. Therefore, tracking data 115 in FIG. 1 can represent data obtained from a plurality of tracking technologies. For example, tracking data 115 can include a position and/or orientation of a medical device relative to a reference point obtained from a first tracking technology, a stress measurement obtained by a second tracking technology, image data obtained by a third tracking technology, and/or a time measurement. Once tracking unit 110 has obtained tracking data 115, tracking unit 110 can communicate tracking data 115 to memory 130.

As tracking data 115 from a plurality of tracking technologies may be stored at memory 130, registration unit 120 may make more than one request for tracking data 115 from more than one tracking technology. Therefore, registration unit 120 may communicate a plurality of tracking data 115 requests to CPU 150 in order for CPU 150 to obtain the proper tracking data 115 from memory 130. In this way, CPU 150 may act as a processor that communicates tracking data 115 between memory 130 and registration unit 120.

In another embodiment, tracking data 115 obtained by all active tracking technologies may be automatically communicated to registration unit 120. In such an embodiment, as tracking data 115 is obtained, it is communicated to registration unit 120 without requiring a request to be communicated from registration unit 120 to memory 130.

Memory 130 may be embodied in any computer-readable memory. Tracking data 115 can be stored on memory 130. The storage of tracking data 115 allows for system 100 to archive tracking data 115 for later use. For example, as tracking data 115 may include data from a plurality of tracking technologies, not all of tracking data 115 may be immediately useful. Therefore, the storage of tracking data 115 at memory 130 can allow for the immediate use of some tracking data 115 and the storage for later use of other tracking data 115, for example.

One or more of CPU 150 and registration unit 120 may obtain tracking data 115 from memory 130. CPU 150 can include any computer processor with embedded or loadable software. CPU 150 may be capable of receiving tracking data 115 requests from registration unit 120, accessing memory 130 to obtain tracking data 115, and communicating tracking data 115 to registration unit 120.

For example, registration unit 120 may communicate a tracking data request to CPU 150 along a registration unit-CPU communication path 125. Once CPU 150 receives the data request, CPU 150 may then obtain the requested tracking data 115 from memory 130 along CPU-memory communication path 155, for example. Memory 130 can communicate the requested tracking data 115 to CPU 150 along communication path 155, for example. CPU 150 may then communicate requested tracking data 115 along communication path 125, for example.

Registration unit 120 can include any device capable of creating and communicating tracking data 115 requests, receiving tracking data 115 and processing tracking data 115. For example, registration unit 120 may include a computer processor capable of receiving measured dipole moments from one or more electromagnetic ("EM") coils in an EM tracking system and processing these dipole moments into a position and/or orientation of a medical instrument relative to a coil array. In another example, registration unit 120 may receive tracking data 115 including image data. Registration unit 120 may include a computer processor capable of processing image data to create an image to be displayed on display device 140, for example.

Registration unit 120 integrates tracking data 115 from at least one tracking technology, image data, and one or more patient coordinates into a single coordinate system. The image data may include an image of a patient or a patient anatomy acquired by an imaging device (such as a C-arm x-ray device, for example) or a graphic representation of the patient or patient anatomy. The image data may be previously obtained and stored at memory 130 or may be obtained during a medical procedure.

In an example, registration unit 120 may receive tracking data 115 from one tracking technology. Registration unit 120 then registers tracking data 115 with the image data in order provide conformity with a patient coordinate system. Registration unit 120 may register tracking data 115 with the image data by transforming the coordinate system of tracking data 115 and or the image data's coordinate system so that the various coordinate systems relate appropriately.

In another example, registration unit 120 may receive a plurality of tracking data 115 from a plurality of tracking technologies (as described below). The tracking technologies may have different coordinate systems and therefore tracking data 115 with respective coordinate systems that do not match each other or the image data. Registration unit 120 may therefore register tracking data 115 from a first active tracking technology with tracking data 115 from a second active tracking technology. Registration unit 120 then registers tracking data 115 from the first and second active tracking technologies with the image data. As described in more detail below, tracking data 115 from one or more active tracking technologies may be weighted relative to tracking data 115 from one or more other active tracking technologies, for example.

In another embodiment, registration unit 120 may first register tracking data 115 from a first active tracking technology with the image data, followed by registering tracking data 115 from a second active tracking technology with the image data. In any one of the above embodiments, registration unit 120 can therefore register tracking data 115 from differing coordinate systems to a single common coordinate system.

Registration unit 120 may also register tracking data 115 (from one or more tracking technologies) and/or image data with a patient coordinate system. Registration unit 120 may register image data by a user, such as a surgeon, identifying one or more points of a patient and/or patient anatomy on an image of the patient and/or anatomy displayed on display device 140. Tracking data 115 may be registered with the patient coordinate system before or after image data is registered with the patient coordinate system.

In another embodiment, registration unit 120 may register image data with the patient coordinate system by projecting an image (representative of the image data) onto the patient during surgery or a medical procedure.

Once registration unit 120 has requested, received and processed tracking data 115, registration unit 120 can then communicate output data along communication path 125 to CPU 150. CPU 150 may then further process the output data before communicating it to memory 130 or CPU 150 may communicate the output data to memory 130 without any further processing. The communication of the output data from CPU 150 to memory 130 can occur over communication path 155, for example.

Once memory 130 receives the output data, memory 130 can store the output data for later use or send the output data along communication path 135 to display device 140 for display. Once display device 140 receives the output data, display device 140 may display a representation based on at least the output data to one or more users of system 100. Display device 140 can include, for example, any device capable receiving data from memory 130 to be displayed. For example, display device 140 may include a computer screen. A representation of output data may include, for example, a graph based on tracking data 115, information related to tracking data 115 overlaid on a stored image, volume rendering based on at least tracking data 115, or an image.

In another embodiment of the present invention, one or more of display device 140, memory 130, CPU 150 and registration unit 120 may be embodied in a single physical unit.

In another embodiment of the present invention, tracking data 115 can include an in situ measurement. An in situ measurement can include any measurement not about the instrument itself. For example, an operator may want real-time, in situ information about the tissue parameters such as hardness or density to determine whether to excise the tissue during an oncology-related surgical procedure. As another example, it could be advantageous to determine the tissue temperature in situ during an ablation procedure so that normal tissue damage is minimized. As another example, during a cardiac surgery, the surgeon may want real-time, in situ information about the electrical potential at a given cardiac location to improve surgical confidence.

In another embodiment of the present invention, tracking data 115 can include timing data. As multiple tracking technologies may be employed (as described below), response times of two or more tracking technologies may differ. In addition, tracking data 115 from one tracking technology may be delayed. In either case, tracking data 115 may build up and not be processed in a regular manner. In order to correct for this, tracking data 115 can include timing data or a time stamp for each tracking technology, for example. When memory 130 receives the time stamp of tracking data 115 and communicates the tracking data 115 and time stamp to registration unit 120, registration unit 120 can compare time stamps from a plurality of tracking technologies. By comparing the time stamps from tracking data 115 of the plurality of tracking technologies and matching the time stamps to each other or to a clock in registration unit 120, tracking data 115 from the plurality of tracking technologies may be registered accordingly, for example.

In another embodiment of the present invention, display device 140 can display a plurality of representations where each representation is based on at least tracking data 115 obtained by a different tracking technology of tracking unit 110.

Figure 2:
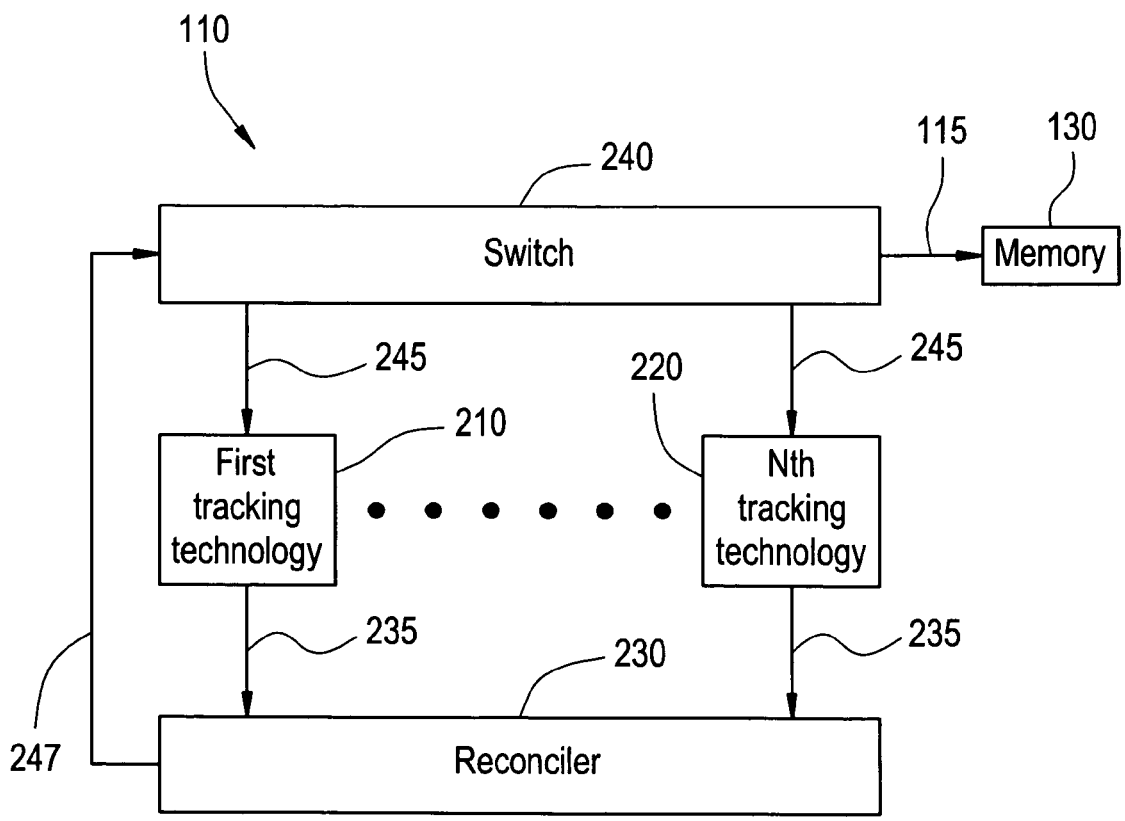
FIG. 2 illustrates the tracking unit used in accordance with an embodiment of the present invention.

FIG. 2 illustrates tracking unit 110 used in accordance with an embodiment of the present invention. Tracking unit 110 includes a plurality of tracking technologies, a reconciler 230, and a switch 240. The plurality of tracking technologies includes a first tracking technology 210 and an Nth tracking technology 220. However, the plurality of tracking technologies may include more than first and Nth tracking technologies 210, 220. References made to tracking technologies 210, 220 may include greater or fewer numbers of tracking technologies.

First and Nth tracking technologies 210, 220 communicate with reconciler 230 and switch 240. Reconciler 230 communicates with first and Nth tracking technologies 210, 220 and with switch 240. Switch 240 communicates with first and Nth tracking technologies 210, 220, reconciler 230, and with memory 130.

In operation, one or more of the plurality of tracking technologies are employed in a medical procedure to obtain tracking data 115. For example, first tracking technology 210 may be used to track a position and/or orientation of a hip implant in a hip-replacement surgery. A tracking technology currently in use can be considered an active tracking technology. An active tracking technology can include more than one of the tracking technologies in the plurality of tracking technologies. For example, an active tracking technology can include first tracking technology 210 (tracking position and/or orientation data of an implant or instrument) and a second tracking technology (obtaining an image of a patient's anatomy).

Tracking technologies 210, 220 can include any device capable of obtaining tracking data 115 in a medical procedure. For example, one or more of tracking technologies can include an optical infrared camera system, a video camera system, an EM system, a sonic or spark gap system, a fiber optic system, a magnetic system an ultra-wide band ("UWB") system, a strain gauge, an accelerometer/gyroscope system, or any combination of the above.

Figure 6A:
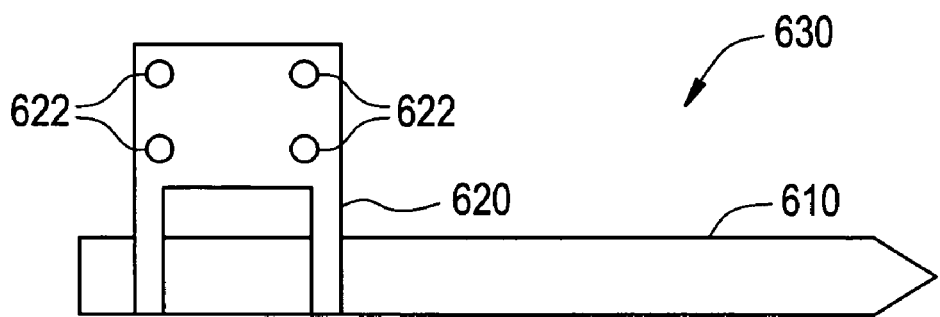
FIGS. 6A and 6B illustrate an exemplary medical instrument with an attached or imbedded tracking sensor.
Figure 6B:
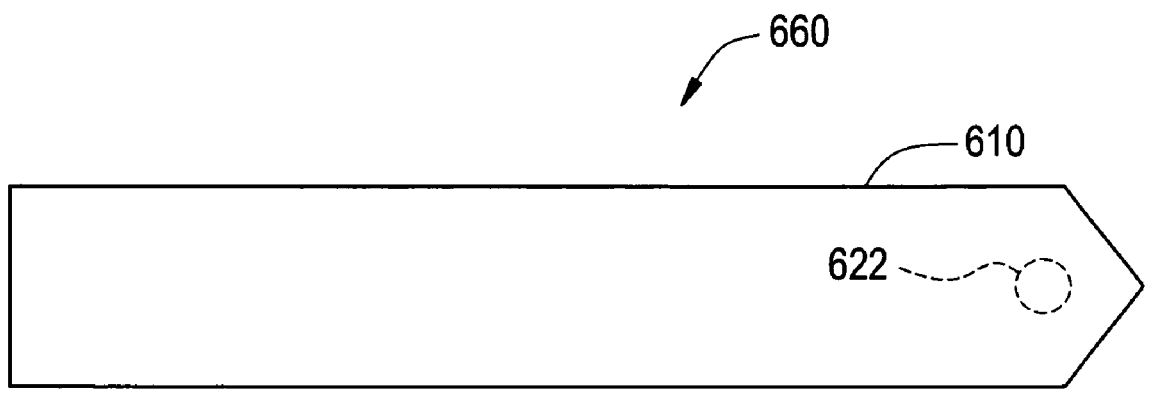
Figure 6B:
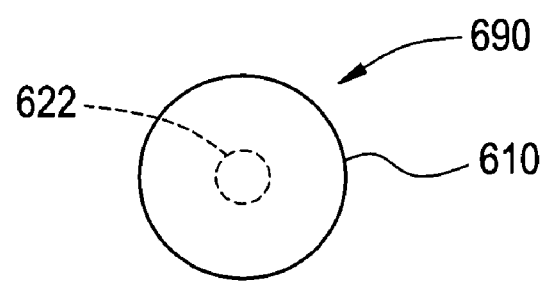

One or more of tracking technologies 210, 220 can be embedded in or attached to an instrument or implant. FIGS. 6A and 6B illustrate an exemplary medical instrument 610 with an attached or imbedded tracking sensor 622, respectively. Instrument 610 and sensors 622 shown in FIGS. 6A and 6B are provided merely to illustrate an example of an embodiment of the present invention and not intended as a limitation on the present invention. FIG. 6A includes a side plan view 630 of instrument 610 with an attachment 620. Instrument 610 may be an external medical probe, for example. Attachment 620 may be removably or permanently attached to instrument 610. Attachment 620 can include an array of sensors 622. Sensors 622 may include, for example, electromagnetic transmitting sensors, for example.

FIG. 6B includes a side plan view 660 and a front view 690 of instrument 610. Instrument 610 includes an embedded sensor 622, as illustrated by the dashed outline of sensor 622 in both views 660 and 690. Sensor 622 may be embedded in the material of instrument 610 during production of instrument 610, for example.

For example, a tracking technology may be embedded in the instrumentation of, or be in the form of an external probe or attachment to, an anatomical fixation (for example, an attachment of a reference to the anatomy, either directly to the patient via a rigid or semi-rigid mechanism or to an operative environment), a probe, a drill, a surgical guide (such as a shunt, biopsy, or drill, for example), a catheter, a stimulator, a debrider, an aspirator, a curette, forceps, a bovi, a microscope, a U/S probe, an endoscope, or any implant (such as pins, screws, plates, or artificial joints, for example).

As one or more tracking technologies 210, 220 obtain tracking data 115, tracking data 115 may be communicated to reconciler 230 via communication path 235. In addition, one or more of tracking technologies 210, 220 may measure a metric associated with the tracking technology. For example, in a hybrid optical/EM system, the reconciler may measure signal-to-noise ratio (SNR) of tracking systems and the switch may be initiated if an SNR associated with the optical tracking system falls below a threshold while the EM tracking system remains above its respective SNR threshold. As yet another example, a threshold metric can be based on running signal statistics (for example, a local variance, running average, or a ratio of running average to local standard deviation).

In addition, a metric may include a comparison between tracking data 115 obtained by an activated tracking technology and a calibration signal, for example. A calibration signal may include an expected response or measurement from the active tracking technology. In this way, the metric may include a comparison of an actual response to an expected response and assist in the determination of how close the two responses are to each other. The measured metric(s) can be communicated from tracking technologies 210, 220 to reconciler 230 via communication paths 235.

Reconciler 230 determines which tracking technologies 210, 220 are to be activated and which are to be deactivated at any given time. Reconciler 230 may base this decision on at least one or more of tracking data 115 (obtained by tracking technology 210, 220) and a metric (measured by tracking technology 210, 220).

For example, reconciler 230 may determine one or more tracking technologies 210, 220 based on at least an optimization of metrics measured by and/or tracking data 115 obtained by tracking technologies 210, 220. When a metric associated with a deactivated tracking technology exceeds a metric associated with an active tracking technology, reconciler 230 may direct switch to activate the tracking technology with the greater metric and deactivate the tracking technology with the lesser metric. In this way, reconciler 230 may activate and/or deactivate one or more tracking technologies 210, 220 automatically.

For example, if $k_1$, $k_2$ and $k_3$ represent metrics associated with first, second and third tracking technologies, respectively, then reconciler 230 may monitor $k_1$, $k_2$ and $k_3$. If reconciler 230 determines that $k_2$ is larger than $k_1$ and $k_3$, then reconciler 230 may direct switch 240 to activate the second tracking technology. Similarly, if at a later time reconciler 230 determines that $k_3$ now exceeds both $k_2$ and $k_1$, then reconciler 230 may direct switch 240 to activate the third tracking technology, deactivate the second tracking technology, and keep the first tracking technology deactivated.

In addition, if more than one deactivated tracking technology includes a metric greater than an active tracking technology, then reconciler 230 may determine which tracking technology has the greatest metric associated with it. For example, if the third tracking technology is activated and the first and second tracking technologies are deactivated, and reconciler 230 determines that both $k_1$, and $k_2$ exceed $k_3$, then reconciler 230 may direct switch 240 to deactivate the third tracking technology. In addition, reconciler 230 may also determine the greater of $k_1$ and $k_2$ and direct switch 240 to activate the corresponding tracking technology.

System 100 may therefore alternate between one or more tracking technologies 210, 220 as a need may arise during a medical procedure. As described above, current multi-technology tracking systems merely allow for an operator to determine one or more switch-over points in a procedure before the procedure begins. Such current systems do not allow for an operator to switch between one or more tracking technologies based on a need as it arises during a medical procedure. For example, an operator may not realize, prior to a surgery, that an optical tracking technology is not the most accurate tracking technology at various points in the procedure. By employing system 100, the operator may switch from the optical tracking technology to an EM tracking technology when the operator realizes that the EM technology results in increased tracking accuracy, for example.

In another embodiment of the present invention, reconciler 230 may activate a deactivated tracking technology when a metric associated with the deactivated technology exceeds a metric associated with an activated tracking technology for a threshold period of time.

In another embodiment of the present invention, reconciler 230 may direct switch 240 to activate a plurality of tracking technologies with the largest metrics. For example, reconciler 230 may determine that both $k_1$ and $k_3$ are larger than $k_2$. Therefore, reconciler 230 may direct switch 240 to activate the first and third tracking technologies, regardless of the comparison between $k_1$, and $k_3$.

In another embodiment of the present invention, reconciler 230 may base the determination of which tracking technology (ies) 210, 220 to activate and/or deactivate on at least one or more of patient factors, the type of medical procedure, a measurement of an amount of remaining consumable and the type of medical instrument or implant employed in the procedure. Patient factors can include, for example, one or more physical characteristics of a patient. An amount of remaining consumable can include, for example, a measurement of a remaining fuel source for one or more components of system 100.

In another embodiment of the present invention, reconciler 230 may provide a notification to an operator of system 100 when one or more metrics fall below a threshold amount. For example, if first and second metrics associated with first and second tracking technologies measure an accuracy of the tracking technologies, then reconciler 230 can notify the operator when one or more of the accuracy metrics fall below a threshold amount. An accuracy metric of a tracking technology can include, for example, a comparison between tracking data 115 obtained by the tracking technology and a calibration signal. The calibration signal may be based on at least expected tracking data 115, for example.

The notification can include any audio, visual, or tactile indicators and/or any combination thereof capable of obtaining the attention of the operator. For example, the notification can include audible beeping, the flashing of lights on instrumentation or display device 140, and/or a text message displayed on display device 140.

In another embodiment of the present invention, reconciler 230 may provide a notification to an operator of system 100 when metrics associated with all available and/or currently used tracking technologies 210, 220 fall below a threshold amount. For example, if first and second metrics associated with first and second tracking technologies measure an accuracy of the tracking technologies, then reconciler 230 can notify the operator when both of the accuracy metrics fall below a threshold amount.

In another embodiment of the present invention, metrics associated with various tracking technologies are compared in a normalized fashion.

Reconciler 230 may include a human operator of system 100, electronic hardware, or a software application. Reconciler 230 may also include any combination of a human operator, electronic hardware and a software application.

For example, reconciler 230 may include electronic hardware including electronic circuitry (or set of circuitry) capable of determining when to activate and/or deactivate one or more tracking technologies 210, 220. Reconciler 230 may direct the activation and/or deactivation of tracking technologies 210, 220 by communicating at least one of activation and deactivation signals to switch 240. Activation and deactivation signals may be communicated to switch 240 via communication path 247. For example, in a hybrid optical/EM tracking system, electronic circuitry of reconciler 230 may monitor noise in tracking data 115 obtained by the optical system and direct switch 240 to activate the EM tracking system when the noise reaches a threshold level.

In another example, reconciler 230 may include a software application embedded in or loadable onto a processor. The software application may be capable of directing switch 240 to activate or deactivate one or more of tracking technologies 210, 220. For example, in a hybrid optical/EM tracking system, when a certain software procedure is initiated on the software application of reconciler 230, the software application may direct switch 240 to activate the EM tracking system 210 and deactivate the optical tracking system 220. For example, in a spinal surgery, the surgeon initiates the surgery with optical tracking and when the field of view becomes obscured (for example, a line of sight is no longer possible), the surgeon switches tracking to EM. The switching to EM allows the surgeon to have an improved location and orientation of the instrument instead of total obliviousness.

Reconciler 230 may also include a human operator. The operator may decide when to activate one tracking technology 210, 220 and deactivate another. For example, in a hybrid optical/EM tracking system, the operator may decide that a current portion of the medical procedure requires EM tracking. Therefore, the operator may direct switch 240 to activate the EM tracking technology and deactivate the currently used optical tracking technology via a manual input. Such a decision may occur, for example, when the operator realizes that line of sight tracking, typically required for optical tracking, is not possible.

As described above, reconciler 230 communicates at least one of activation and deactivation signals to switch 240 via communication path 247. In addition, tracking data 115 from one or more tracking technologies 210, 220 may also be communicated to switch 240 via communication path 247.

An activation and/or deactivation signal may be associated with a single or multiple tracking technologies. For example, reconciler 230 may communicate an activation signal and a deactivation signal. The activation signal may direct switch 240 to activate first tracking technology 210 while the deactivation signal may direct switch 240 to deactivate Nth tracking technology 220, for example. However, a single activation/deactivation signal may activate and/or deactivate more than one tracking technology.

Once switch 240 receives an activation signal, switch 240 can direct a corresponding tracking technology 210, 220 to begin actively obtaining tracking data 115, as described above. For example, an activation signal may direct switch 240 to turn on a tracking technology 210 that was previously off and not obtaining any data 115.

In another embodiment of the present invention, once switch 240 receives an activation signal, switch 240 can begin communicating tracking data 115 for a corresponding tracking technology 210, 220 to memory 130, as described above. For example, first and Nth tracking technologies 210, 220 may each be obtaining tracking data 115 even though first tracking technology 210 is in an activated state and Nth tracking technology 220 is in a deactivated state. Switch 240 may therefore be communicating tracking data 115 from first tracking technology 210 to memory 130 and not be communicating tracking data 115 from Nth tracking technology 220 to memory 130. Once switch 240 receives an activation signal for Nth tracking technology 220, switch 240 may begin communicating tracking data 115 from Nth tracking technology 220 to memory 130, for example.

Once switch 240 receives a deactivation signal, switch 240 can direct one or more tracking technologies to either stop obtaining tracking data 115 or switch 240 can prevent one or more representations (based on at least output data communicated from memory 130 to display device 140, which is in turn based on at least tracking data 115, as described above) from being displayed on display device 140. For example, switch 240 can prevent a representation from being displayed by ceasing to communicate tracking data 115 to memory 130. In another embodiment, switch 240 may communicate a signal to display device 140 directing display device 140 to stop displaying one or more representations based on at least tracking data 115 from one or more tracking technologies 210, 220. While display device 140 may cease displaying a representation based on tracking data 115 obtained by a first tracking technology 210, for example, first tracking technology 210 may continue to obtain tracking data 115.

Switch 240 may include one or more of a human operator of system 100, electronic hardware, or a software application. Switch 240 may also include any combination of a human operator, electronic hardware and a software application.

For example, switch 240 may include electronic hardware including electronic circuitry (or set of circuitry) capable of receiving an activation and/or deactivation signal and activating at least one tracking technology 210, 220 and/or deactivating another.

In another example, switch 240 may include a software application embedded in or loadable onto a processor. The software application may be capable of initiating a software protocol that activates at least one tracking technology 210, 220 and/or deactivates another upon receipt of an activation and/or deactivation signal.

Switch 240 may also include a human operator. The operator may decide when to switch from one or more tracking technologies 210, 220 to another by physically indicating an activation and/or deactivation. Such a physical indication can include the pushing of a button or the attachment or removal of a tracking device from a medical instrument or implant, for example.

Switch 240 may activate one or more tracking technologies 210, 220 automatically. For example, switch 240 may activate first tracking technology 210 without any feedback from a user or operator of system 100. In an exemplary hybrid optical/EM tracking system, for example, system 100 may automatically activate the EM tracking technology when optical tracking is unavailable. The determination that optical tracking is unavailable may be based, for example, on a metric such as the visibility of markers attached to a patient or reference point, for example.

Figure 3A:
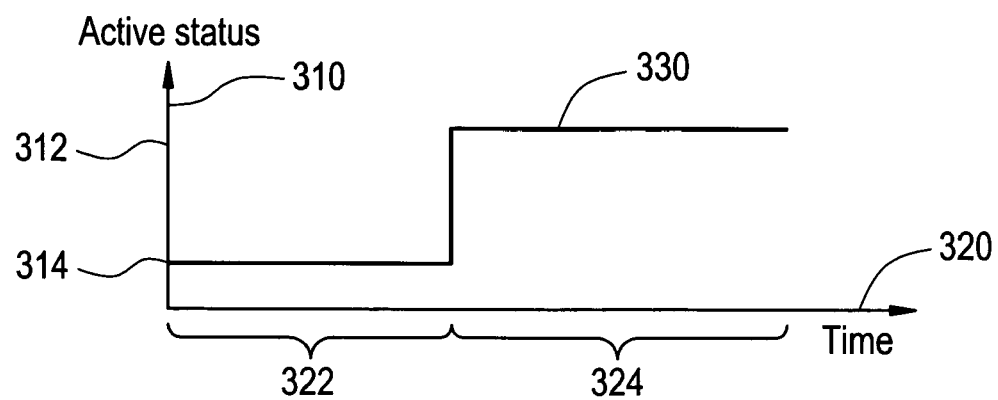
FIGS. 3A, 3B and 3C illustrate three exemplary switching techniques used in accordance with an embodiment of the present invention.
Figure 3B:
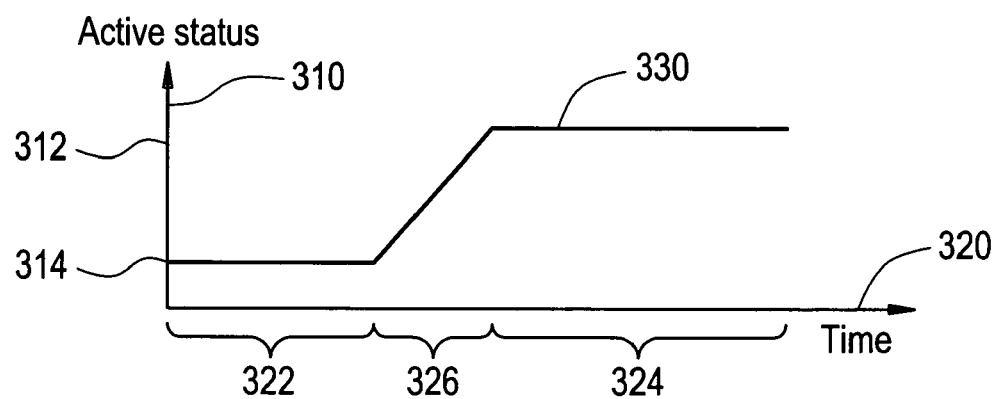
Figure 3C:
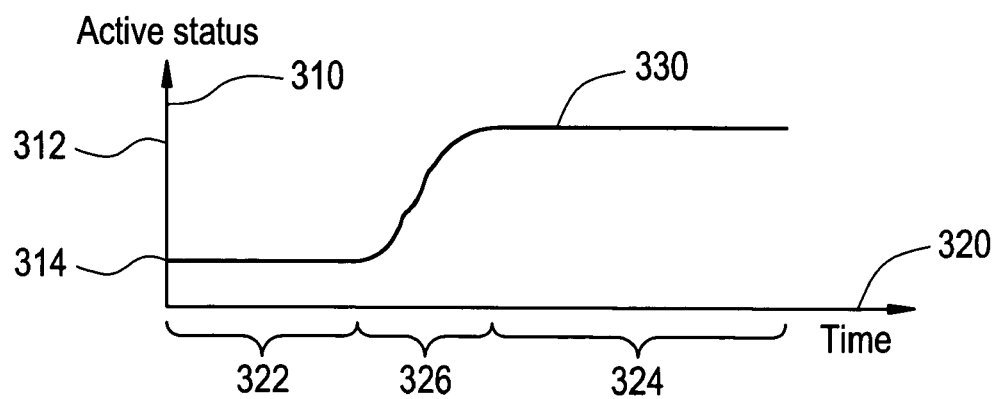

Switch 240 may activate and/or deactivate one or more tracking technologies 210, 220 by direct switching or weighted switching. FIGS. 3A, 3B and 3C illustrate three exemplary switching techniques used in accordance with an embodiment of the present invention. Each of FIGS. 3A, 3B and 3C include an active status axis 310, a time axis 320, and a switching relationship 330. Active status axis 310 includes two points, namely a deactivated status point 314 and an activated status point 312. Deactivated status point 314 represents a point at which one or more tracking technologies 210, 220 are deactivated, as described above. Activated status point 312 represents a point at which one or more tracking technologies 210, 220 are activated. FIGS. 3A, 3B and 3C also include at least two time periods, namely a first tracking technology 210 deactivation time period 322 and a first tracking technology 210 activation time period 324. Relationship 330 represents the activated or deactivated status of first tracking technology 210. However, relationship 330 may represent the activated/deactivated status of additional tracking technologies.

During time period 322, first tracking technology 210 is in a deactivated state, as illustrated by point 314. At some time prior to the end of time period 322 and the beginning of time period 324, reconciler 230 communicates an activation signal to switch 240 directing switch 240 to activate first tracking technology 210. Therefore, switch 240 activates first tracking technology 210 instantaneously, as illustrated by the change of relationship 330 from deactivated point 314 to activated point 312 at the beginning of time period 324. The instantaneous activation of first tracking technology 210 may include the activation of technology 210 within a relatively short period of time after switch 240 receives the activation signal, such as 3 second or less, for example.

As first tracking technology 210 may be directly activated as shown in FIG. 3A, a second tracking technology may be directly deactivated. For example, the second tracking technology may be in an activated state 312 during time period 322 and then be instantaneously switched to a deactivated state 314 at the beginning of time period 324.

Direct switching can result in a first representation (corresponding to tracking data 115 from first tracking technology 210) to switch from not being displayed at all on display device 140 to being instantaneously displayed on display device 140 at the beginning of time period 324, for example. Similarly, a second representation (corresponding to tracking data 115 from a second tracking technology) to switch from being displayed on display device 140 to not being displayed on display device 140 instantaneously at the beginning of time period 324, for example. Therefore, display device 140 may display the first representation during time period 322 and instantly cease to display the first representation and begin displaying the second representation at the beginning of time period 324.

As described above, before displaying a representation based on at least tracking data 115 from a first tracking technology 210, tracking data 115 must be registered with image data relating to an image of a patient or patient anatomy. In the situation where only one tracking technology 210 is actively measuring tracking data 115 at any one given time (for example, a static tracking system), tracking data 115 is registered with the image data. Such a situation may occur with direct switching, for example.

In order to register tracking data 115 with the image data, a coordinate system for the tracking technology 210 (that measured tracking data 115) is transformed to match a coordinate system for the image data. For example, if a user is employing an optical tracking system (as first tracking technology 210) to measure first tracking data 115, the coordinate system for the optical tracking system is registered with the image coordinate system. A representation based on at least first tracking data 115 may then be displayed on display device 140.

In another embodiment of the present invention, switch 240 may employ weighted switching as exemplified in FIGS. 3B and 3C. Weighting switching includes the gradual activation of one or more tracking technologies 210, 220. Similar to FIG. 3A, relationship 330 in FIGS. 3B and 3C includes first time period 322 where first tracking technology 210 is in a deactivated state 314 and second time period 324 where first tracking technology 210 is in an activated state 312. Relationship 330 in FIGS. 3B and 3C also includes a transition time period 326, occurring after first time period 322 and before second time period 324.

During transition time period 326, switch 240 can activate first tracking technology 210 gradually. Switch 240 may direct display device 140 to gradually increase the display of one or more representations based on at least tracking data 115 obtained by first tracking technology 210. For example, display device 140 may gradually increase the brightness of a representation (corresponding to first tracking technology 210) displayed on device 140.

Similarly, during transition time period 326, switch 240 can also deactivate a second tracking technology gradually. Switch 240 may direct display device 140 to gradually decrease the display of one or more representations based on at least tracking data 115 obtained by the second tracking technology. For example, display device 140 may gradually decrease the brightness of a representation (corresponding to the second tracking technology) displayed on device 140. By gradually "fading out" a representation from a first tracking technology 210 and "fading in" a representation from a second tracking technology, weighted switching can provide a seamless display on device 140 of a tracked probe, instrument or implant when the switching from the first technology to the second technology occurs.

In another embodiment of the present invention, the gradual switching over from the display of a first representation to a second representation is non-linear, as shown in FIG. 3C.

In another embodiment of the present invention, relationship 330 (defining weighted switching) may vary for each switching possibility and/or surgical protocol. For example, in the gradual switching from optical to EM tracking technologies, a gradual, non-linear switching may occur (as exemplified by relationship 330 of FIG. 3C). During the same medical procedure, in a later switch between the EM tracking technology to a sonic tracking system, an instantaneous switching may occur (as exemplified by relationship 330 of FIG. 3A), for example.

In another embodiment of the present invention, reconciler 230 and switch 240 are integrated into a single physical unit. For example, reconciler 230 and switch 240 may both be included into a single processing unit.

Figure 7:
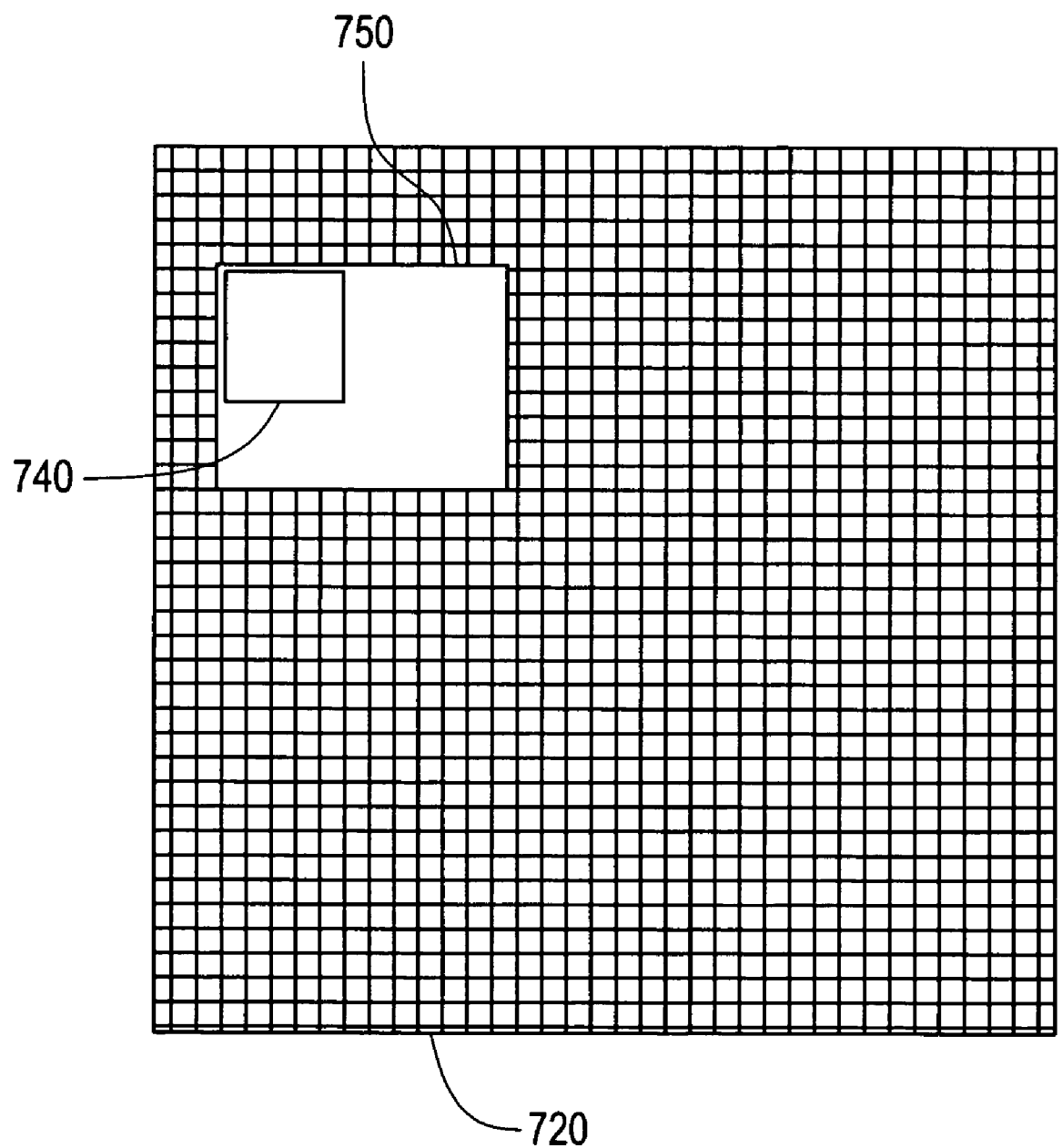
FIG. 7 illustrates an image coordinate system displaying a position of a medical instrument using a more accurate tracking technology to improve the accuracy of a lesser accurate tracking technology according to an embodiment of the present invention.

In another embodiment of the present invention, in a situation where a plurality of tracking technologies 210, 220 are actively measuring tracking data 115 (for example, a dynamic tracking system) and weighted switching is employed, tracking data 115 from a first tracking technology 210 may be used to increase the accuracy of tracking data 115 from a second tracking technology 220. FIG. 7 illustrates an image coordinate system 720 displaying a position 740, 750 of a medical instrument using a more accurate tracking technology to improve the accuracy of a lesser accurate tracking technology according to an embodiment of the present invention. Image coordinate system 720 is a schematic diagram of the coordinate system to which tracking data 115 from first tracking technology 210 and from a second tracking technology 220. Positions 740, 750 represent areas in which the medical instrument may be located in image coordinate system 720 as measured by first and second tracking technologies 210, 220, respectively.

As described above, a first tracking technology 210 may be activated and be measuring first tracking data 115. As described above, first tracking data 115 may be registered with image data coordinate system 720, for example. First tracking data 115 may be used to determine a position 740 of medical instrument 730.

At a given point in time, it may be desirous to switch from first tracking technology 210 to the second tracking technology 220. For example, a user may be employing an optical tracking technology until an optical tracker becomes occluded. At this point, the user may switch from the optical tracking technology (for example, the first tracking technology 210) to an EM tracking technology (for example, the second tracking technology 220).

The second tracking technology 220 may then obtain second tracking data 115 to determine a position 750 of the medical instrument. However, as evident from FIG. 7 and the corresponding difference in size between positions 740 and 750, the second tracking technology 220 may be less accurate than the first tracking technology 210. However, registration unit 120 may use a last known position to improve the accuracy of position 750. For example, registration unit 120 may use position 740 (measured by a more accurate tracking technology 210) to narrow the possible area where a medical instrument is located as measured by the second, less accurate tracking technology 220. In this way, registration unit 120 may limit the position of the medical instrument displayed on display device 140 and as measured by the second tracking technology 220 to position 740, instead of position 750.

In another embodiment of the present invention, system 100 may be calibrated before, during and/or after a medical procedure. System 100 may be calibrated by any method known to those of ordinary skill in the art. For example, system 100 may be calibrated by placing a fiducial marker on a patient. Then, one or more tracking technologies 210, 220 may be put into contact with the marker while the tracking technologies are obtaining tracking data 115. Using the known marker point and the measured tracking data 115, a user may calibrate system 100.

Figure 4:
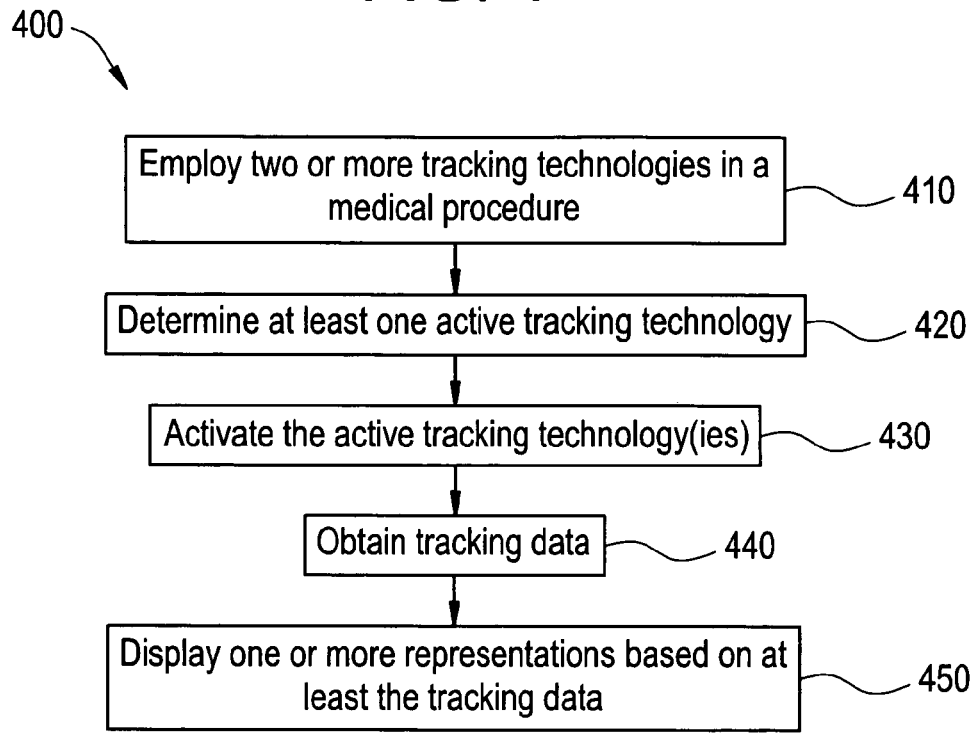
FIG. 4 illustrates a flowchart for a method for hybrid tracking in a medical navigation system in accordance with an embodiment of the present invention.

FIG. 4 illustrates a flowchart for a method 400 for hybrid tracking in a medical navigation system in accordance with an embodiment of the present invention. First, at step 410, a plurality of tracking technologies 210, 220 are employed in a medical procedure. Both technologies 210, 220 need not, but may be obtaining tracking data 115 during the procedure simultaneously.

Next, at step 420, at least one of tracking technologies is determined to be an active tracking technology. As described above, this determination may occur based on a comparison of metrics associated with, and/or tracking data 115 obtained by, tracking technologies 210, 220. At step 430, the tracking technology 210, 220 determined to be the active tracking technology is activated. As described above, more than one tracking technology 210, 220 may be activated.

Next, at step 440, the activated tracking technology(ies) obtains tracking data 115. At step 450, the tracking data 115 obtained by the activated tracking technology(ies) is employed to generate at least one representation. The representation(s) are then displayed on display device 140, as described above.

In another embodiment of the present invention, at step 430, one or more tracking technologies 210, 220 are deactivated. For example, at step 430 a first tracking technology 210 may be activated while a second tracking technology may be deactivated.

In another embodiment of the present invention, at step 440, one or more deactivated tracking technologies 210, 220 may continue to obtain tracking data 115. The tracking data 115 obtained by the deactivated technologies 210, 220 may be withheld from communication to memory 130 or may be withheld from being used to generate one or more representations displayed at step 450, for example.

Figure 5:
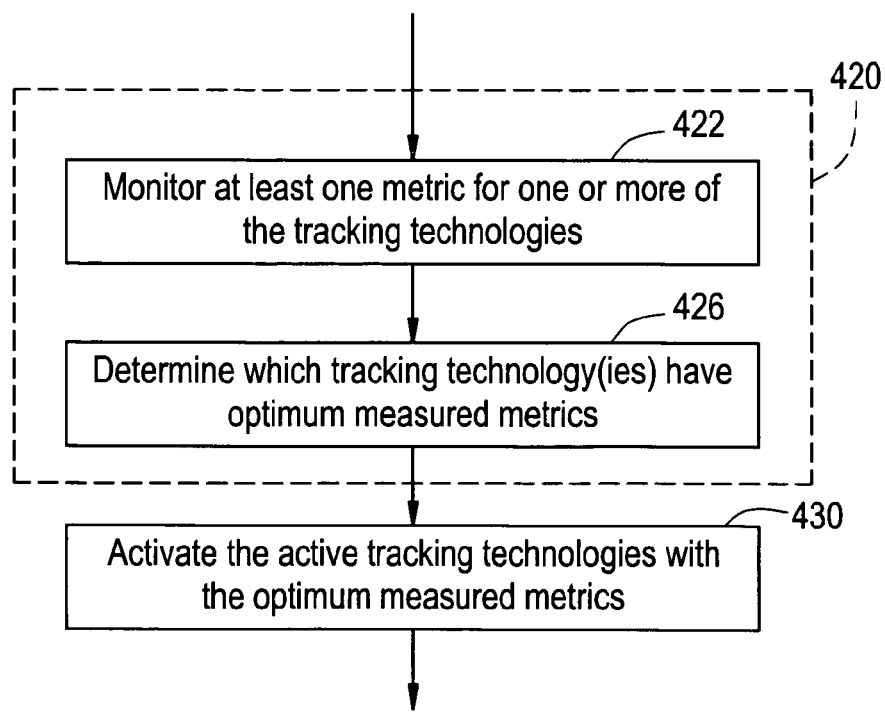
FIG. 5 illustrates another embodiment of the flowchart of method according to an embodiment of the present invention.

FIG. 5 illustrates another embodiment of the flowchart of method 400 according to an embodiment of the present invention. FIG. 5 includes steps 420 and 430 of method 400. In addition, step 420 in FIG. 5 includes two additional steps 422, 426. Thus, as shown in FIG. 5, method 400 may proceed from step 410 to step 422, to step 426 and to step 430.

Step 422 includes monitoring at least one metric associated with one or more tracking technologies 210, 220. For example, a metric may include an accuracy measurement, as described above. Next, at step 426 (also included within step 420), a determination is made as to which tracking technology(ies) has optimum measured metrics. As described above, this determination may include a normalized comparison of all metrics measured by tracking technologies 210, 220 in order to determine the largest metric(s), for example. The determination may also include a comparison between a metric measured by an activated tracking technology and metrics measured by deactivated tracking technologies.

Next, at step 430, the tracking technology with the largest metric (as determined in step 426) is activated. As described above, if a deactivated tracking technology has a larger metric than an activated metric, then the deactivated tracking technology may become activated and the activated tracking technology may become deactivated, for example. Moreover, also as described above, if more than one deactivated tracking technologies have larger metrics than an activated metric, then step 430 may activate the tracking technology with the largest metric or all tracking technologies with metrics larger than the activated tracking technology, for example While particular elements, embodiments and applications of the present invention have been shown and described, it is understood that the invention is not limited thereto since modifications may be made by those skilled in the art, particularly in light of the foregoing teaching. It is therefore contemplated by the appended claims to cover such modifications and incorporate those features that come within the spirit and scope of the invention.

What is claimed is:

1. A medical tracking system, said system including:
   a plurality of tracking technologies employed during a medical procedure;
   a reconciler determining an active tracking technology during said procedure, said active tracking technology including at least one of said tracking technologies;
   a switch activating said active tracking technology, wherein said switch activates said active tracking technology over a period of time such that a visual representation corresponding to said active tracking technology becomes more visible as a visual representation corresponding to said deactivated tracking technology becomes less visible over said time period; and
   wherein each tracking technology has a metric associated therewith, and, when a metric associated with a deactivated tracking technology exceeds a metric associated with an activated tracking technology, said reconciler directs said switch to activate the tracking technology with the greater metric and deactivate the tracking technology with the lesser metric.

2. The system of claim 1, wherein said active tracking technology determines tracking data for at least one of a medical instrument and implant.

3. The system of claim 2, wherein said tracking data includes timing data.

4. The system of claim 3, wherein said timing data is employed to synchronize said tracking data with tracking data measured by a second active tracking technology.

5. The system of claim 2, further including a display presenting a representation based on at least said tracking data.

6. The system of claim 1, wherein said switch deactivates at least one of said tracking technologies by causing a display device to cease displaying a representation based on at least tracking data measured by said at least one tracking technology.

7. The system of claim 1, wherein said switch includes at least one of electronic circuitry receiving at least one of activation and deactivation signals from said reconciler and a processor having a software application stored thereon.

8. The system of claim 1, wherein said switch activates said active tracking technology instantaneously.

9. The system of claim 1, wherein said reconciler includes at least one of electronic circuitry communicating at least one of activation and deactivation signals to said switch and a processor having a software application stored thereon.

10. A method for hybrid tracking in medical navigation system, said method including:
    employing a plurality of tracking technologies for use during a medical procedure;
    determining an active tracking technology during said procedure, said active tracking technology including at least one of said tracking technologies;
    activating said active tracking technology, wherein said activating step occurs over a period of time such that a visual representation corresponding to said active tracking technology becomes more visible as a visual representation corresponding to said deactivated tracking technology becomes less visible over said time period; and
    wherein each tracking technology has a metric associated therewith, and, when a metric associated with a deactivated tracking technology exceeds a metric associated with an activated tracking technology, said activating step includes activating the tracking technology with the greater metric and deactivating the tracking technology with the lesser metric.

11. The method of claim 10, further including measuring tracking data for at least one of a medical instrument and implant.

12. The method of claim 11, further including displaying a representation based on at least said tracking data.

13. The method of claim 10, wherein said tracking data includes timing data.

14. The method of claim 13, further including synchronizing said tracking data with tracking data measured by a second active tracking technology.

15. The method of claim 10, wherein said activating step includes activating said active tracking technology during said procedure.

16. The method of claim 10, further including deactivating at least one of said tracking technologies, said deactivating including ceasing to display a representation based on at least tracking data measured by said at least one tracking technology.

17. The method of claim 10, wherein said activating step is completed by at least one of electronic circuitry receiving at least one of activation and deactivation signals from said reconciler and a processor having a software application stored thereon.

18. The method of claim 10, wherein said activating step occurs instantaneously.

19. The method of claim 10, wherein said determining step is performed by at least one of electronic circuitry communicating at least one of activation and deactivation signals to said switch and a processor having a software application stored thereon.

20. The method of claim 10, further including monitoring a metric associated with each of said tracking technologies, wherein said determining step is based on at least an optimization of said metrics.

21. A system for optimizing an accuracy of navigation in a medical procedure, said system including:
    first and second tracking systems used in said procedure;
    a monitor measuring first and second accuracies of said first and second tracking systems, respectively; and
    a switch activating said first tracking system and deactivating said second tracking system when said first accuracy measurement is greater than said second accuracy measurement.

22. The system of claim 21, wherein said switch activates said first tracking system automatically.

23. The system of claim 22, further including a display gradually presenting a representation associated with tracking data from said first tracking system after activation and gradually removing an image associated with tracking data from said second tracking system after deactivation.

24. he system of claim 23, further including an alarm notifying a user of said system when said first and second accuracies decrease below a threshold amount.

* * * * *

UNITED STATES PATENT AND TRADEMARK OFFICE
CERTIFICATE OF CORRECTION

PATENT NO. : 7,702,379 B2  Page 1 of 1
APPLICATION NO. : 10/926380
DATED : April 20, 2010
INVENTOR(S) : Avinash et al.

It is certified that error appears in the above-identified patent and that said Letters Patent is hereby corrected as shown below:

Col. 16, line 46, claim 24, delete "he" and insert --the--.

Signed and Sealed this

Ninth Day of November, 2010

David J. Kappos
*Director of the United States Patent and Trademark Office*